US012805893B2

(12) United States Patent
Sharma et al.

(10) Patent No.: US 12,805,893 B2
(45) Date of Patent: Nov. 24, 2026

(54) REUSABLE HANDLES FOR MEDICAL SYSTEMS AND DEVICES, AND RELATED METHODS OF USE

(71) Applicant: Boston Scientific Medical Device Limited, Galway (IE)

(72) Inventors: Deepak Kumar Sharma, Muzaffarnagar (IN); Aditya Dhanotiya, Indore (IN); Subodh Morey, Ponda (IN); Shrikant Vasant Raut, Mumbai (IN); Nachiket Gole, Pune (IN); Pooja Bhuvanesh Kulkarni, Pune (IN)

(73) Assignee: Boston Scientific Medical Device Limited, Galway (IE)

( * ) Notice: Subject to any disclaimer, the term of this patent is extended or adjusted under 35 U.S.C. 154(b) by 61 days.

(21) Appl. No.: 18/883,698

(22) Filed: Sep. 12, 2024

(65) Prior Publication Data

US 2025/0090188 A1 Mar. 20, 2025

Related U.S. Application Data

(60) Provisional application No. 63/582,861, filed on Sep. 15, 2023.

(51) Int. Cl.
*A61B 17/29* (2006.01)
*A61B 17/00* (2006.01)

(52) U.S. Cl.
CPC .................... *A61B 17/2909* (2013.01); *A61B 2017/00469* (2013.01); *A61B 2017/2902* (2013.01); *A61B 2017/2946* (2013.01); *A61B 2017/2947* (2013.01)

(58) Field of Classification Search
CPC ...... A61B 17/2909; A61B 2017/00464; A61B 2017/0046; A61B 2017/291
See application file for complete search history.

(56) References Cited

U.S. PATENT DOCUMENTS 6,569,105 B1 5/2003 Kortenbach et al.
7,311,674 B2 * 12/2007 Gingrich ................ A61B 10/06 600/564
2013/0037595 A1 * 2/2013 Gupta .............. A61B 17/07207 227/176.1
2019/0183504 A1 * 6/2019 Shelton, IV ..... A61B 17/07207
2022/0087703 A1 3/2022 Sharma et al.

FOREIGN PATENT DOCUMENTS

EP 2777562 A1 9/2014

* cited by examiner

*Primary Examiner* — Christina C Lauer
(74) *Attorney, Agent, or Firm* — Bookoff McAndrews PLLC

(57) ABSTRACT

A medical device that includes a handle including a first body and a second body that are movable relative to one another, and an actuator including a first housing movably coupled to the first body and a second housing movably coupled to the second body. The medical device is configured to move between an open configuration in which the first body is at least partially decoupled from the second body and the first housing is at least partially decoupled from the second housing, and a closed configuration in which the first body is coupled to the second body and the first housing is coupled to the second housing.

20 Claims, 8 Drawing Sheets

REUSABLE HANDLES FOR MEDICAL SYSTEMS AND DEVICES, AND RELATED METHODS OF USE

CROSS-REFERENCE TO RELATED APPLICATIONS

This application claims the benefit of priority to U.S. Provisional Application No. 63/582,861, filed on Sep. 15, 2023, which is incorporated by reference herein in its entirety.

TECHNICAL FIELD

Various aspects of the disclosure generally relate to reusable handles of medical systems and devices, and related methods for utilizing the reusable handles to treat a subject (e.g., a patient). In particular, aspects of the disclosure relate to reusable medical systems, devices, and methods for selectively attaching and detaching a medical tool to a reusable handle device for use in treating a target treatment site (e.g., a wound) within the subject.

BACKGROUND

Medical devices intended for single-use generally involves disposing the device in its entirety, despite portions of the device, such as the handle(s), not being subjected to the unsterile conditions or environments, unlike those portions of the medical device that are received within a subject and positioned at a target treatment site in the subject. Such single-use medical devices may generally include plastic handles that are discarded after use, thereby increasing an environmental footprint resulting from the use of the medical device. Disposable medical devices generally include a single handle design that does not provide a flexibility and/or an interchangeability for different users having varying hand profiles or sizes, thus causing ergonomic concerns in the use of such devices. Disposable medical devices may further lead to increased costs due to a need for replacing the medical device in its entirety after each single use. The systems, devices, and methods of the current disclosure may rectify one or more of the deficiencies described above or address other aspects of the art.

SUMMARY

Each of the aspects disclosed herein may include one or more of the features described in connection with any of the other disclosed aspects.

Aspects of the disclosure relate to, among other things, systems, devices, and methods for treating a subject. Aspects of this disclosure relate to reusable handles of medical systems and devices, and methods for selectively attaching and detaching a medical tool to the reusable handle for use in treating a subject.

According to an example, a medical device comprising a handle including a first body and a second body that are movable relative to one another; and an actuator including a first housing movably coupled to the first body and a second housing movably coupled to the second body; wherein the medical device is configured to move between an open configuration in which the first body is at least partially decoupled from the second body and the first housing is at least partially decoupled from the second housing, and a closed configuration in which the first body is coupled to the second body and the first housing is coupled to the second housing.

Any of the medical devices described herein may include any of the following features. The first body and the second body collectively define a channel that is configured to receive a medical tool when the medical device is in the open configuration. The medical tool is securely attached inside the channel between the first body and the second body when the medical device is in the closed configuration. An end effector of the medical tool is movably coupled to the actuator when the medical tool is received within the channel and the medical device is in the closed configuration. The actuator is configured to actuate the end effector in response to the first housing and the second housing moving simultaneously along the first body and the second body. The end effector is configured to move in response to the actuator translating along the first body and the second body. The first body and the second body are movably coupled to one another about a joint. The medical device including a first hinge defining the joint, wherein the first hinge is configured to pivot the first body relative to the second body relative. The joint is a first joint and the medical device includes a second hinge defining a second joint, wherein the first hinge and the second hinge are collectively configured to pivot the first body and the second body relative to one another. The first hinge is positioned proximate to a proximal end of the first body and the second body relative to the second hinge, and the second hinge is positioned proximate to a distal end of the first body and the second body relative to the first hinge. The medical device including a first locking mechanism configured to couple the first body and the second body to one another, thereby securing the medical device to the closed configuration. The first locking mechanism includes a snap lock positioned on the first body and a ledge positioned on the second body, the snap lock is configured to engage the ledge to couple the first body to the second body. The medical device including a second locking mechanism that is configured to couple the first body and the second body to one another, thereby securing the medical device to the closed configuration. The first locking mechanism is positioned proximate to a proximal end of the first body and the second body relative to the second locking mechanism, and the second locking mechanism is positioned proximate to a distal end of the first body and the second body relative to the first locking mechanism.

According to another example, a medical device comprising a first handle body; a second handle body movably coupled to the first handle body; a first actuator housing disposed about and movably coupled to the first handle body; and a second actuator housing disposed about and movably coupled to the second handle body; wherein the first handle body and the second handle body define a handle of the medical device, and the first actuator housing and the second actuator housing define an actuator of the medical device; and wherein the first handle body is at least partially separated from the second handle body and the first actuator housing is at least partially separated from the second actuator housing when the medical device is in an open configuration, and the first handle body is engaged with the second handle body and the first actuator housing is engaged with the second actuator housing when the medical device is in a closed configuration.

Any of the medical devices described herein may include any of the following features. The medical device is configured to receive a medical tool between the first handle body and the second handle body when in the open configuration. The medical device is configured to securely attach the medical tool to the first handle body and the second handle body when in the closed configuration. The actuator is configured to actuate the medical tool in response to the first actuator housing moving relative to the first handle body and the second actuator housing moving relative to the second handle body. The medical device including at least one joint defining a pivot point between the first handle body and the second handle body, wherein the at least one joint is configured to pivot the first handle body relative to the second handle body about the pivot point as the medical device moves between the open configuration and the closed configuration. The medical device including at least one locking mechanism configured to attach the first handle body to the second handle as the medical device is moved to the closed configuration.

According to another example, a medical system comprising a medical device including a handle and an actuator disposed over the handle; and a medical tool including a shaft, a pull wire disposed within the shaft, and an end effector coupled to the pull wire; wherein the medical device is configured to couple the medical tool to the handle and the actuator in response to receiving at least a portion of the shaft between a pair of opposing halves of the handle and at least a portion of the pull wire between a pair of opposing halves of the actuator; and wherein the medical device is configured to control the medical tool in response moving the actuator relative to the handle to translate the pull wire relative to the shaft, thereby actuating the end effector.

It may be understood that both the foregoing general description and the following detailed description are exemplary and explanatory only and are not restrictive of the invention, as claimed. As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "distal" refers to a direction away from a user/toward a treatment site, and the term "proximal" refers to a direction toward a user. The terms "downward," "upward," "lower," "upper," "bottom," and "top" may refer to directions relative to the views of the elements shown throughout the drawings. The term "exemplary" is used in the sense of "example," rather than "ideal." The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects of this disclosure and together with the description, serve to explain the principles of the disclosure.

DETAILED DESCRIPTION

Endoscopic and open surgical procedures of the gastrointestinal (GI) tract include, for example, colonic resection, bariatric surgery, esophagectomy, biopsy, endoscopic retrograde cholangiopancreatography, endoscopic submucosal dissection, gastric bypass, and sleeve gastrectomy, among others. Urologic procedures (e.g., endoscopic urologic procedures) of the urinary tract require accessing various locations within a subject, such as the kidneys, ureter, bladder, or urethra, among others. In any of these procedures, a medical tool is generally through the corresponding tract of a subject for positioning at a target treatment site (e.g., a lesion) within the subject.

Embodiments of this disclosure include devices, systems, and methods for utilizing a reusable medical device that is operable for selective attachment and detachment to a medical tool that is received inside the subject. In some embodiments, the reusable medical device may be or may include a handle that facilitates endoluminal placement of the medical tool at a wound site within the subject. The medical tool may include a shaft, a catheter, a scope (e.g., endoscope, bronchoscope, colonoscope, etc.), a tube, or a sheath, which may be inserted into the GI and/or urinary tract. The reusable medical device may include a handle interface for controlling the medical tool and may be positioned outside of the subject. The reusable medical device may be sterilized after use in a procedure and leveraged across multiple medical tools for use in various procedures while providing an intuitive user interface. The medical device may provide a sustainable and reusable handle that facilitates detachment and reattachment to numerous medical tools.

Figure 1:
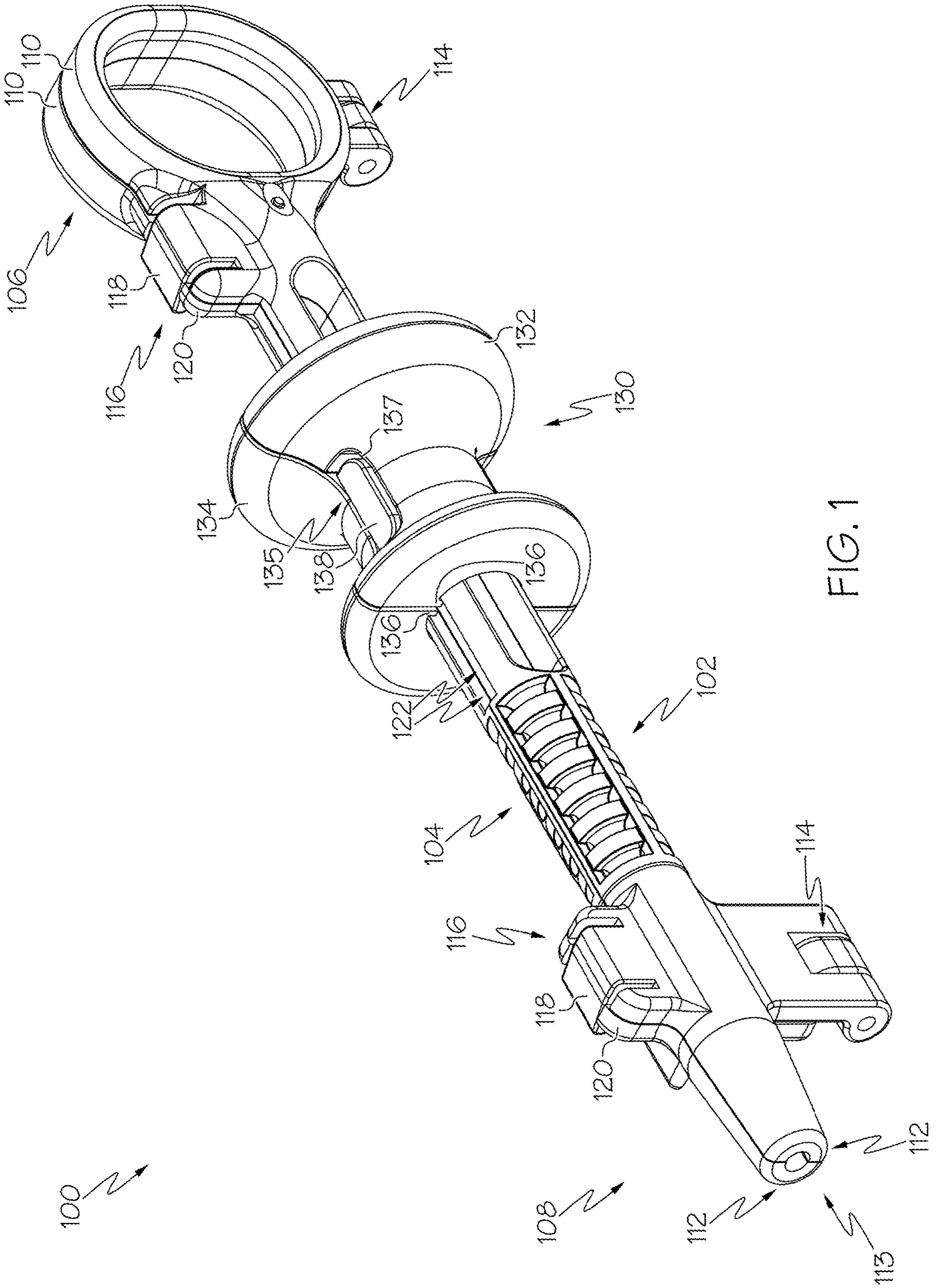
FIG. 1 shows a perspective view of an exemplary medical device in a closed configuration, according to some embodiments.
Figure 2:
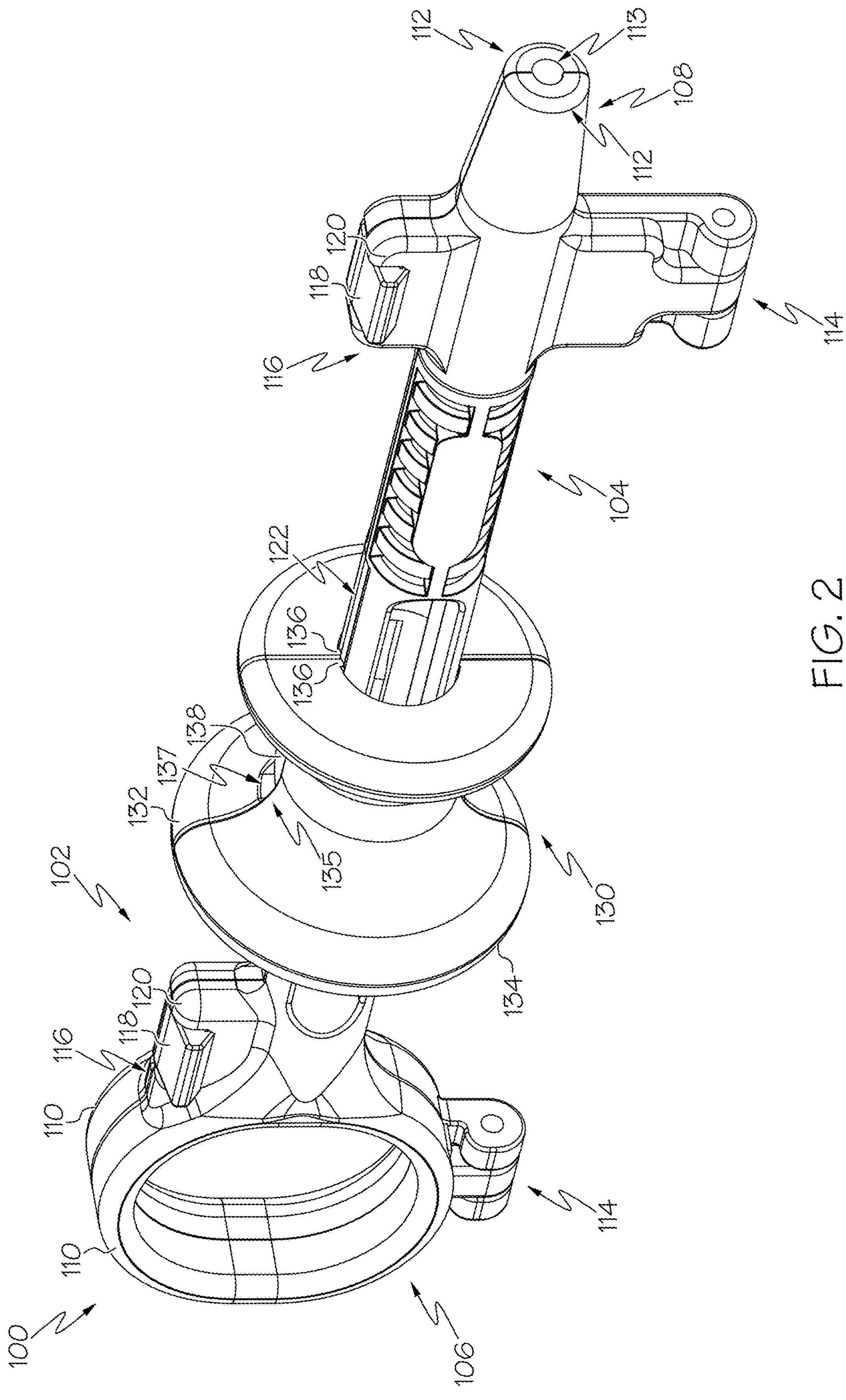
FIG. 2 shows another perspective view of the medical device of FIG. 1 in the closed configuration, according to some embodiments.

FIGS. 1-2 depict an exemplary medical device 100 in a closed configuration. Medical device 100 may define a handle and/or user interface for controlling one or more medical tools or instruments. Medical device 100 may include a first (handle) body 102 and a second (handle) body 104 each having a longitudinal length defined between a proximal end 106 and a distal end 108 of medical device 100. Each of first body 102 and second body 104 may define a respective half of the handle formed by medical device 100. In other words, first body 102 and second body 104 define a pair of opposing halves of the handle. As described herein, the halves of medical device 100 may be selectively attached and detached from one another to couple and decouple at least one medical tool therebetween, respectively. Each of first body 102 and second body 104 may include a handle interface 110 (e.g., a thumb aperture) adjacent to or at proximal end 106. When in the closed configuration, handle interfaces 110 may be in contact and/or positioned adjacent to one another, thereby collectively forming a single handle of medical device 100.

Each of first body 102 and second body 104 may include an outlet 112 (e.g., a semi-circular outlet) adjacent to distal end 108. When in the closed configuration, outlets 112 may be in contact and/or positioned adjacent to one another, thereby collectively forming a single outlet 113 (e.g., a circular outlet) of medical device 100. As described herein, a medical tool received within medical device 100, and particularly between first body 102 and second body 104, may extend distally outwards from distal end 108 via outlets 112. It should be appreciated that outlets 112 may collectively define an opening having a diameter corresponding to a size (e.g., a cross-sectional dimension) of the medical tool. In other embodiments, medical device 100 may include outlets 112 having various other suitable diameters and/or shapes than those shown and described herein without departing from a scope of this disclosure for receiving various other medical tools.

Still referring to FIGS. 1-2, medical device 100 may further include one or more joints 114 configured to movably couple first body 102 and second body 104 to one another. In the example, medical device 100 includes a pair of joints 114, with at least one joint 114 positioned adjacent to proximal end 106 and another joint 114 positioned adjacent to distal end 108. Joints 114 may include hinges and may define a pair of pivot/rotation points between first body 102 and second body 104. Joints 114 may be rotatable/pivotable about one or more axes that are approximately parallel to a central longitudinal axis of medical device 100. Thus, first body 102 and second body 104 may be configured to move relative to one another about the pivot points defined at joints 114. Although a pair of joints 114 are shown and described herein, it should be appreciated that medical device 100 may include additional and/or fewer joints 114 without departing from a scope of this disclosure (see FIG. 6).

Medical device 100 may include one or more locking mechanisms 116 for securely coupling first body 102 to second body 104. Locking mechanisms 116 may be configured and operable to provide a single-step movement for attaching and detaching first body 102 to second body 104. In the example, medical device 100 may include a pair of locking mechanisms 116, with at least one locking mechanism 116 positioned adjacent to proximal end 106 and another locking mechanism 116 positioned adjacent to distal end 108. Each of locking mechanisms 116 may include a snap lock 118 (e.g., a clip) and a ledge 120 (e.g., a tab, a projection, etc.) that is sized, shaped, and/or otherwise configured to receive snap lock 118 for securely coupling first body 102 and second body 104 to one another. In other words, snap lock 118 may be sized, shaped, and/or otherwise configured to engage and/or snap onto ledge 120, thereby attaching first body 102 and second body 104 to one another.

In the example, first body 102 may include snap locks 118 at each of proximal end 106 and distal end 108, and second body 104 may include ledges 120 at each of proximal end 106 and distal end 108, respectively. In other examples, snap locks 118 may be positioned along second body 104 and ledges 120 may be positioned on first body 102. In further examples, each of first body 102 and second body 104 may include at least one snap lock 118 of the pair of snap locks 118 and at least one ledge 120 of the pair of ledges 120. Although a pair of locking mechanisms 116 are shown and described herein, it should be appreciated that medical device 100 may include additional and/or fewer locking mechanisms 116 without departing from a scope of this disclosure (see FIG. 6). In some embodiments, locking mechanisms 116 may be configured and operable to lock and/or unlock first body 102 and second body 104 relative to one another upon moving each of the bodies towards and/or away from one another, respectively.

A plane that is extending along or parallel to a central longitudinal axis of medical device 100 may extend through joints 114 and locking mechanisms 116, such that the plane divides medical device 100 into first body 102 and second body 104. First body 102 and second body 104 may each form a half of medical device 100. Joints 114 may operate to open medical device 100 like a clamshell, as described in further detail below. In some examples, first body 102 and second body 104 may be symmetrical to one another except that one of first body 102 and second body 104 includes snap lock 118 at a given location, and the other of first body 102 and second body 104 includes ledge 120 at the corresponding location for interfacing with snap lock 118 when first body 102 and second body 104 are coupled to one another.

Still referring to FIGS. 1-2, medical device 100 may include at least one rail 122 positioned along a portion of each of first body 102 and second body 104. In the example, the at least one rail 122 on each of first body 102 and second body 104 may extend along an intermediate portion of first body 102 and second body 104, positioned between proximal end 106 and distal end 108 of first body 102 and second body 104, respectively. Rails 122 may be recessed as compared with surrounding portions of first body 102 and second body 104. In some examples, one or more of first body 102 and second body 104 may include multiple rails 122, such as at least one rail 122 formed along a top surface that is proximate to locking mechanisms 116, and at least one rail 122 formed along a bottom surface that is opposite of the top surface and proximate to joints 114.

When in the closed configuration, rails 122 of first body 102 and second body 104 may be in contact and/or positioned adjacent to one another. In examples, in the closed configuration, adjacent rails 122 may form a single slot extending longitudinally along medical device 100. As described herein, rails 122 may be sized, shaped, and/or otherwise configured to receive a corresponding component (e.g., an actuator 130, described below) of medical device 100 for controlling movement of said component (e.g. an actuator). Each rail 122 may have a longitudinal length defining a travel path of the component received thereon. In other words, the longitudinal length of rails 122 may control an extent of longitudinal translation of the component relative to first body 102 and second body 104.

Medical device 100 may include actuator 130 (e.g., a spool) having a first housing 132 and a second housing 134. First housing 132 and second housing 134 may define a pair of opposing halves of actuator 130. Each of first housing 132 and second housing 134 may have various suitable sizes, shapes, and/or configurations. For example, first housing 132 and second housing 134 may include a flange along each opposing end with a recessed portion disposed in between the opposing flanges. It should be appreciated that each of first housing 132 and second housing 134 may have a greater cross-sectional profile along the opposing flanges relative to the recessed portion, respectively.

In the example, first housing 132 may be movably disposed on first body 102 and second housing 134 may be movably disposed on second body 104. As described herein, each housing 132, 134 of actuator 130 may be selectively attached and detached from one another in response to a corresponding attachment and detachment of first body 102 and second body 104 to one another. Furthermore, each housing 132, 134 of actuator 130 may be configured to couple and decouple a medical tool to medical device 100 by receiving at least a portion of the medical tool in between housings 132, 134. Each housing 132, 134 may include a guide 136 (e.g., a projection, a projection, a tab, a finger, etc.) that is sized, shaped, and/or otherwise configured to move along the corresponding rail 122 of first body 102 and second body 104, respectively. In the example, guide 136 of first housing 132 may extend into rail 122 of first body 102, thereby coupling first housing 132 to first body 102. Guide 136 of second housing 134 may extend into rail 122 of second body 104, thereby coupling second housing 134 to second body 104.

Still referring to FIGS. 1-2, each rail 122 may be configured to limit movement of the corresponding guide 136 to a longitudinal direction that coincides with the longitudinal length of rails 122. In some embodiments, rails 122 may be configured to inhibit rotation of actuator 130 relative to first body 102 and second body 104. Furthermore, in the open configuration, discussed below, rails 122 and guides 136 may help to prevent actuators 130 from becoming detached from first body 102 and second body 104. Actuator 130 may have an alignment mechanism 135 that includes one or more slots 137 (e.g., sockets) and one or more projections 138 (e.g., ribs) that are configured to mate with one another when medical device 100 is in the closed configuration. Stated differently, alignment mechanism 135 may be configured to align first housing 132 and second housing 134 with one another when first body 102 is coupled to second body 104, and vice versa, thereby ensuring proper assembly of actuator 103 when medical device 100 is transitioned to the closed configuration. Alignment mechanism 135 may be disposed between the opposing flanges of first housing 132 and second housing 134, such that the respective alignment mechanism 135 may be positioned along the recessed portion of each of first housing 132 and second housing 134.

Figure 3:
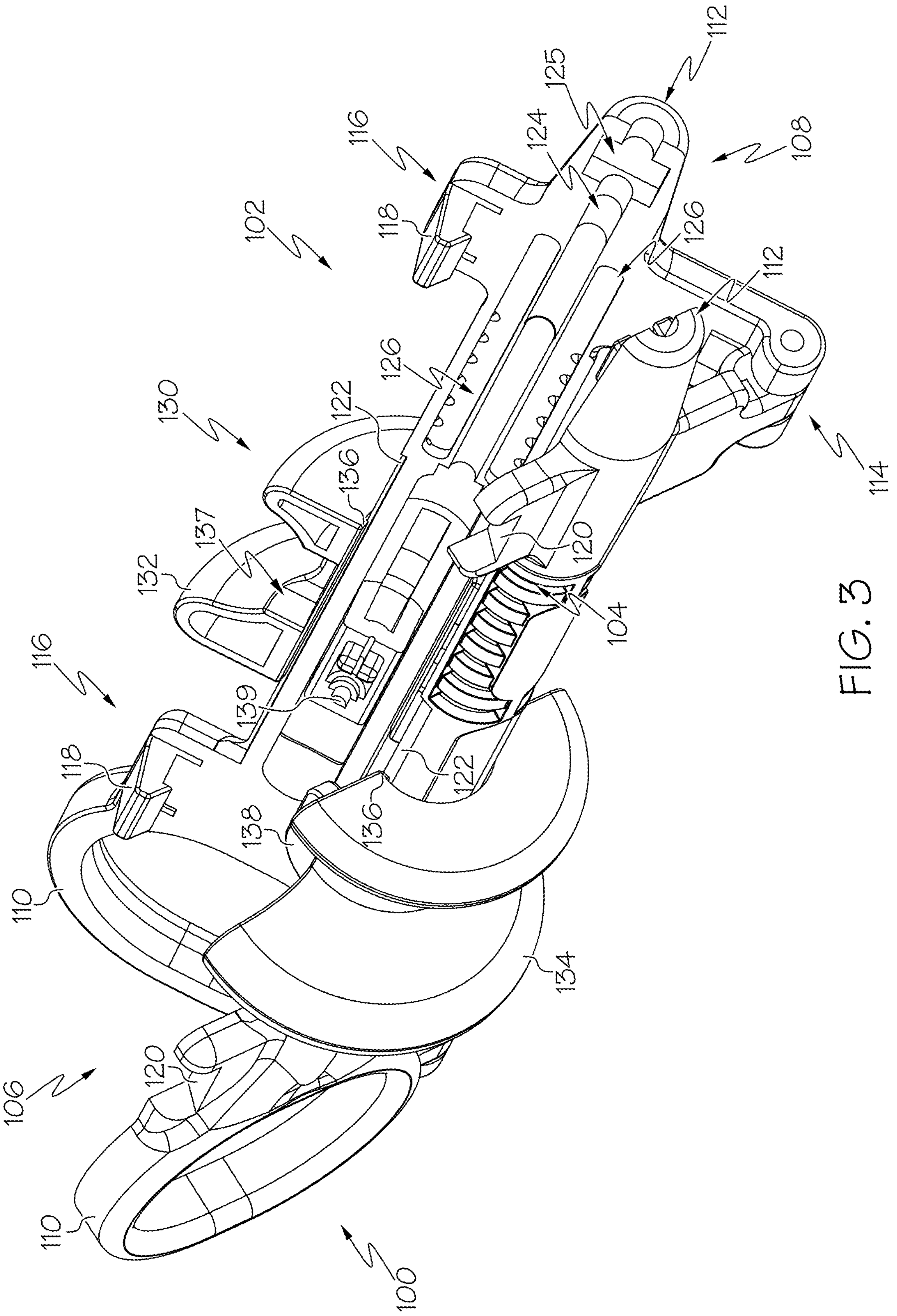
FIG. 3 shows a perspective view of the medical device of FIG. 1 in an open configuration, according to some embodiments.
Figure 4:
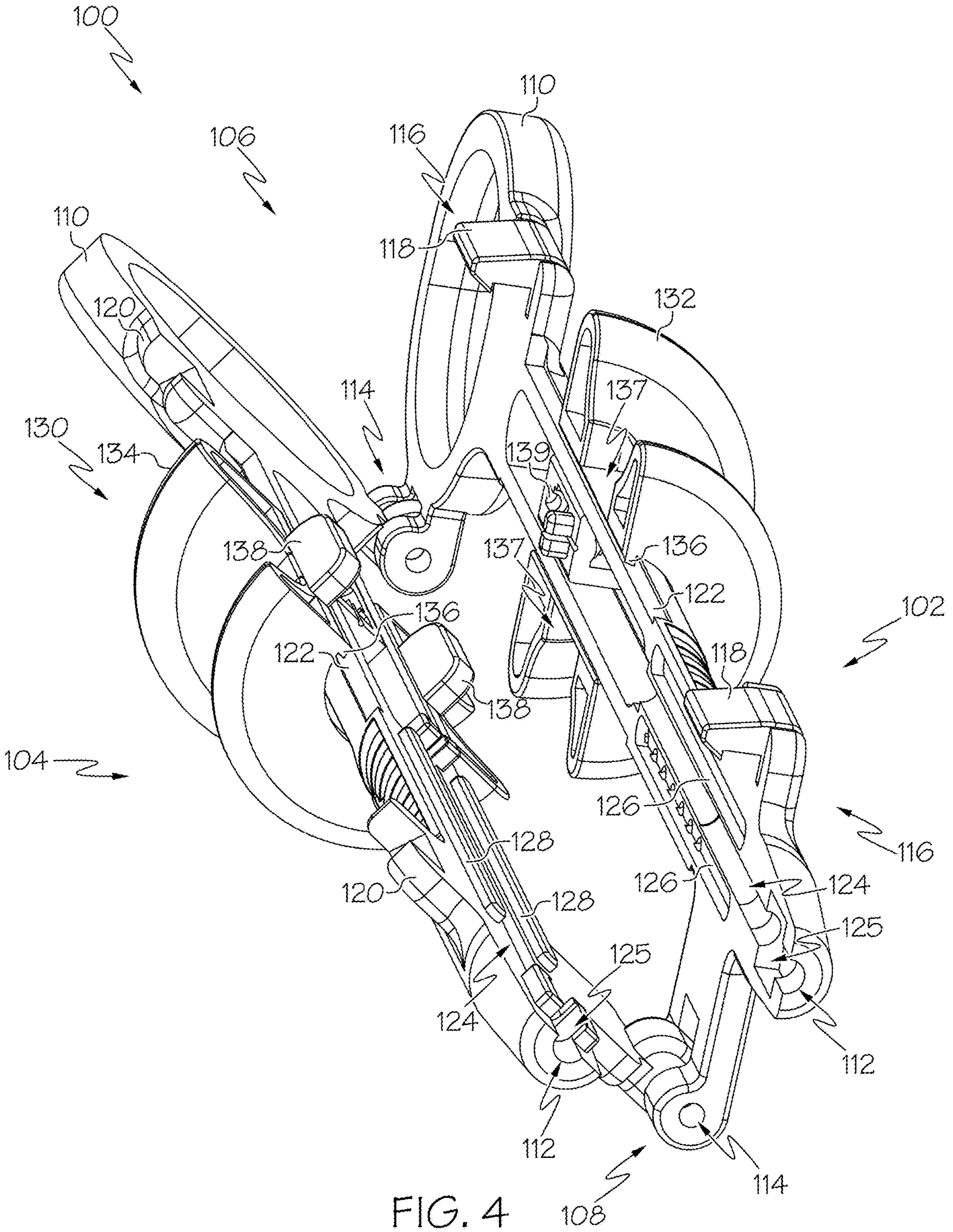
FIG. 4 shows another perspective view of the medical device of FIG. 1 in the open configuration, according to some embodiments.

FIGS. 3-4 depict medical device 100 in an open configuration. In the example, first housing 132 may include a pair of slots 137 and second housing 134 may include a pair of projections 138, as particularly shown in FIG. 4. It should be appreciated that slots 137 may be sized, shaped, and/or otherwise configured to receive projections 138 when first housing 132 is coupled to second housing 134. Alignment mechanism 135 may be configured to inhibit medical device 100 from transitioning to the closed configuration when first housing 132 is not properly aligned with second housing 134 for slots 137 to receive projections 138. In other words, alignment mechanism 135 may inhibit assembly of actuator 130 when first housing 132 is misaligned with second housing 134, and first body 102 is incapable of coupling with second body 104 when first housing 132 and second housing 134 are not properly aligned with one another, i.e. when actuator 130 is not in an assembled state.

In this instance, due to a misalignment of first housing 132 and second housing 134, first body 102 and second body 104 are separated from one another such that locking mechanisms 116 are unable to couple first body 102 and second body 104 to one another. In other embodiments, alignment mechanism 135 may include additional and/or fewer slots 137 and projections 138 than that shown and described herein. Alternatively, it should be appreciated that first housing 132 may include projections 138 and second housing 134 may include slots 137 without departing from a scope of this disclosure.

Still referring to FIGS. 3-4, medical device 100 may include one or more additional alignment mechanisms to further facilitate proper alignment between first body 102 and second body 104 when moving medical device 100 from the open configuration to the closed configuration (FIGS. 1-2). In the example, medical device 100 may include one or more channels 126 (e.g., two channels 126) and one or more protrusions 128 (e.g., two protrusions 128) that are configured to mate with one another when medical device 100 is in the closed configuration. Stated differently, channel(s) 126 and protrusion(s) 128 may be configured to align first body 102 and second body 104 with one another, thereby ensuring proper assembly of medical device 100 when transitioning to the closed configuration.

In the example, first body 102 may include a pair of channels 126 and second body 104 may include a pair of protrusions 128. Alternatively, first body 102 may include both channel(s) 126 and protrusion(s) 128. Second body 104 may include protrusion(s) 128 in position(s) that correspond with channel(s) 126 of first body 102 and channel(s) 126 in position(s) that correspond with protrusion(s) 128 of first body 102. It should be appreciated that channels 126 may be sized, shaped, and/or otherwise configured to receive protrusions 128 when first body 102 is coupled to second body 104. Channels 126 and protrusions 128 may be collectively configured to inhibit medical device 100 from transitioning to the closed configuration when first body 102 is not properly aligned with second body 104 for channels 126 to receive protrusions 128. In other words, the alignment mechanism of channels 126 and protrusions 128 may inhibit assembly of medical device 100 when first body 102 is misaligned with second body 104, such that first body 102 is incapable of coupling with second body 104 in such a misaligned position.

Still referring to FIGS. 3-4, each of first body 102 and second body 104 may include a channel 124 and a first cavity 125 formed along respective interior surfaces of first body 102 and second body 104. First cavities 125 may be positioned adjacent to distal end 108 and disposed between outlets 112 and channels 124, such that channels 124 may be positioned proximal relative to first cavities 125. In some embodiments, channels 124 may include multiple portions with at least a first (distal) portion positioned distally of first cavities 125 and at least a second (proximal) portion positioned proximally of first cavities 125. Channels 124 may generally have a circular and/or semi-circular shape that is configured to receive a first subcomponent of a medical tool therein (e.g., a shaft, a pull wire, and more). First cavities 125 may generally have a squared and/or rectangular shape that is configured to receive a second subcomponent of the medical tool (e.g., a first crimp) for securing the medical tool to medical device 100, and particularly to first body 102 and second body 104.

As described herein, first cavities 125 may be configured to at least partially inhibit movement of one or more portions and/or subcomponents of the medical tool relative to medical device 100, and particularly first body 102 and second body 104, by securing the second subcomponent (e.g., the first crimp) of the medical tool therein. Each of channels 124 may form an opened (partial) lumen when medical device 100 is in the open configuration, and may collectively form an enclosed channel (lumen) that is sized, shaped, and/or otherwise configured to enclose the corresponding (first) subcomponent of the medical tool when medical device 100 is in the closed configuration. Each of first cavities 125 may form an opened (partial) chamber when medical device 100 is in the open configuration, and may collectively form an enclosed chamber that is sized, shaped, and/or otherwise configured to enclose the corresponding (second) subcomponent of the medical tool when medical device 100 is in the closed configuration with first body 102 and second body 104 coupled to one another.

Each of first housing 132 and second housing 134 of actuator 130 may include a second cavity 139 formed along an interior surface of first housing 132 and second housing 134, respectively. Second cavities 139 may generally have a squared and/or rectangular shape that is configured to receive the third subcomponent of the medical tool (e.g., a second crimp) for securing the medical tool to actuator 130, and particularly to first housing 132 and second housing 134. As described herein, second cavities 139 may be configured to movably couple one or more portions and/or subcomponents of the medical tool to actuator 130, by securing the third subcomponent (e.g., the second crimp) of the medical tool therein. Each of second cavities 139 may form an opened (partial) chamber when medical device 100 is in the open configuration, and may collectively form an enclosed chamber that is sized, shaped, and/or otherwise configured to enclose the corresponding (third) subcomponent of the medical tool when medical device 100 is in the closed configuration.

Figure 5A:
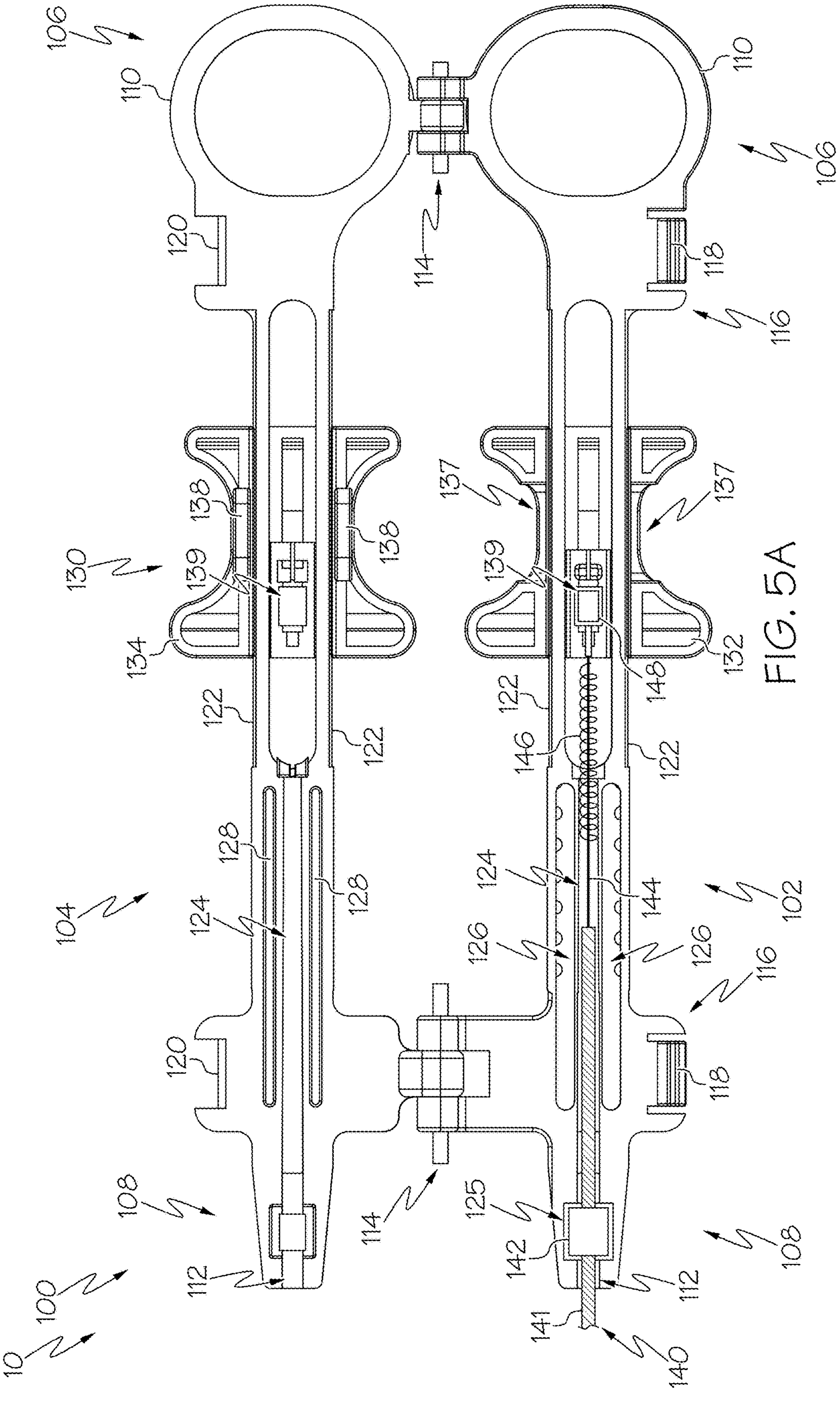
FIG. 5A shows a top view of the medical device of FIG. 1 in the open configuration for receiving a medical tool, according to some embodiments.
Figure 5B:
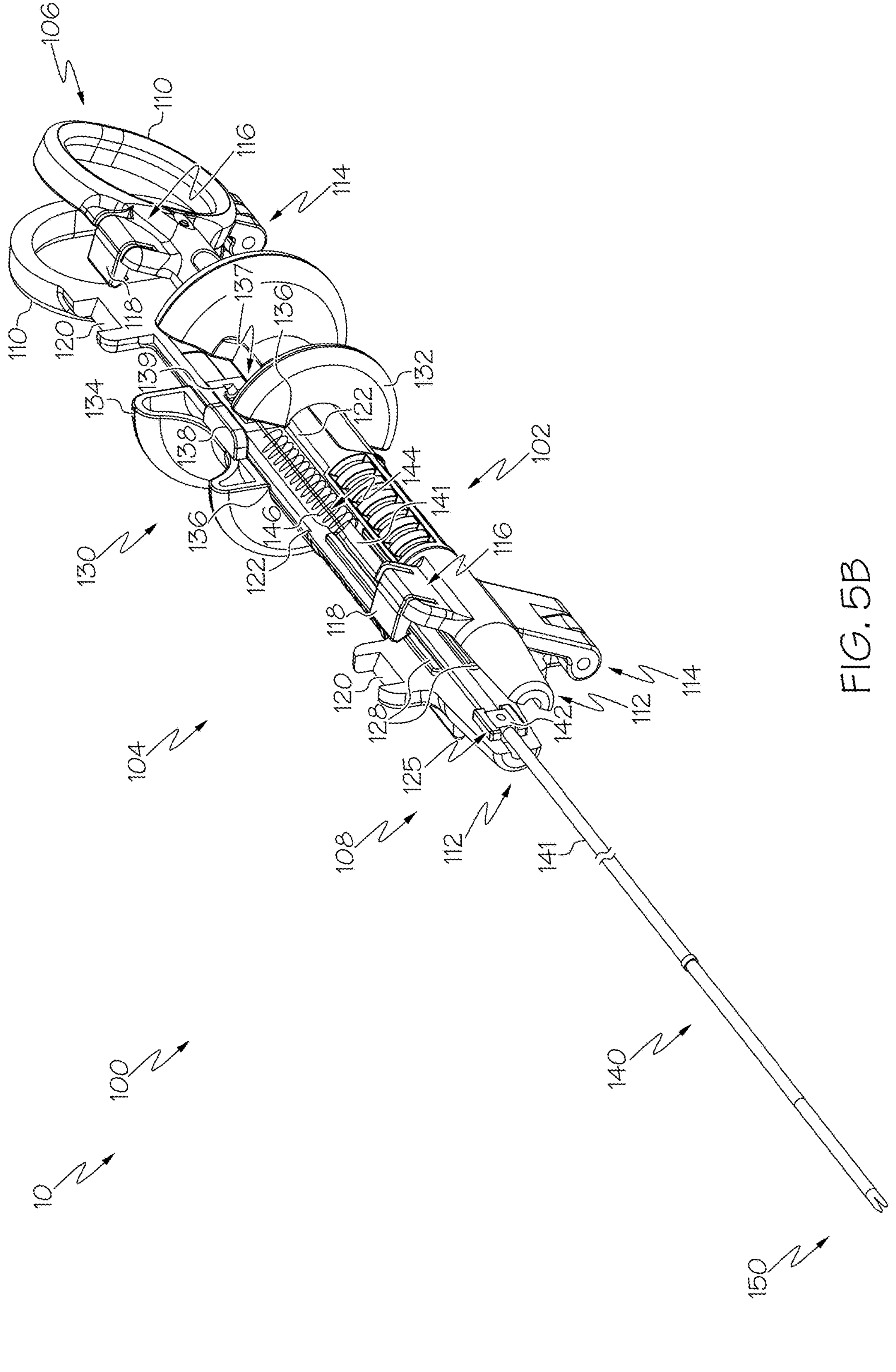
FIG. 5B shows a perspective view of the medical device of FIG. 1 in a partially closed configuration for securing the medical tool therein, according to some embodiments.
Figure 5C:
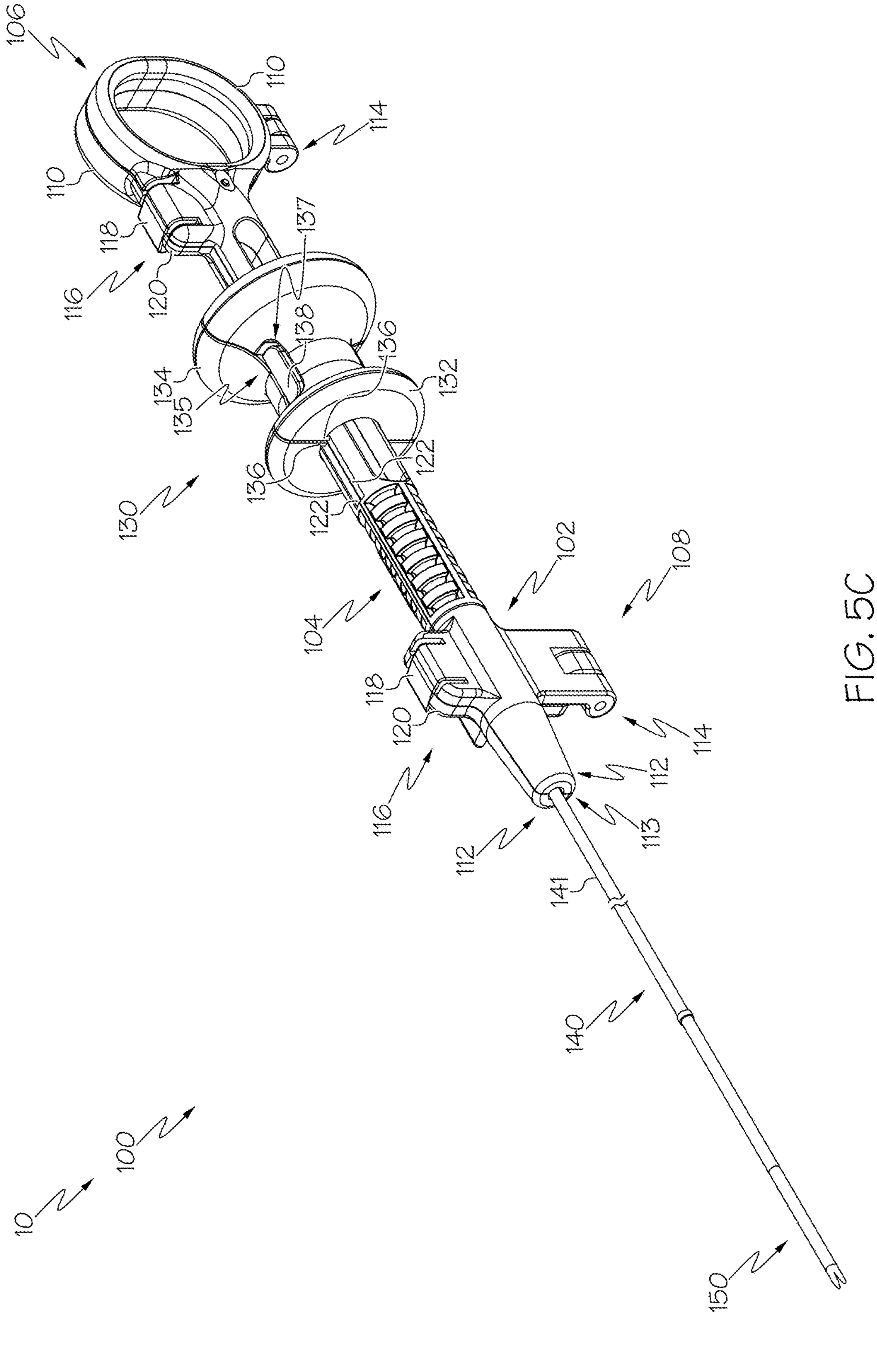
FIG. 5C shows a perspective view of the medical device of FIG. 1 in the closed configuration for coupling with the medical tool, according to some embodiments.

In exemplary use, as shown in FIGS. 5A-5C, medical device 100 may be utilized to treat a subject (e.g., a patient) by facilitating control of one or more medical tools at a target treatment site within the subject. For example, referring specifically to FIG. 5A, medical device 100 may be configured to receive a medical tool 140 within at least one of first body 102 and second body 104 when medical device 100 is in an open configuration. In the example, medical tool 140 is initially received within first body 102. Medical tool 140 may include various suitable instruments, devices, and/or tools. In the example, medical tool 140 may include a shaft 141, a pull wire 144, and a biasing mechanism 146 (e.g., a spring, such as a coil spring) received within channel 124 of first body 102. Shaft 141 may extend distally from channel 124 via outlet 112 of first body 102. As describe further below, a distal end of medical tool 140 may include one or more end effectors 150 or other elements which may be actuated by, for example, pull wire 144. Pull wire 144 may be at least partially disposed within shaft 141 and at least partially exposed outside of shaft 141 within channel 124. For example, pull wire 144 may extend proximally from a proximalmost end of shaft 141, which may be disposed inside channel 124. Pull wire 144 may be movable proximally and distally with respect to shaft 141 and channel 124.

Medical tool 140 may include a first crimp 142 (or other protruding element) along a portion of shaft 141, and first cavity 125 may be sized, shaped, and/or otherwise configured to receive first crimp 142 for securely fixing shaft 141 to first body 102 (and second body 104 when first crimp 142 is received within the corresponding first cavity 125 of second body 104). In this instance, first cavity 125 may inhibit longitudinal translation of first crimp 142 relative to first body 102 (and second body 104), such that shaft 141 may be longitudinally fixed relative to first body 102 (and second body 104). In some embodiments, first crimp 142 may have a squared and/or rectangular cross-sectional profile that corresponds to a cross-sectional profile of first cavities 125. First crimp 142 may have a larger width than a width of portions of channel 124 that are proximal and distal of first cavity 125, such that first crimp 142 is retained within first cavity 125 and inhibited from moving into channel 124.

Medical tool 140 may further include a second crimp 148 (or other protruding element) at a proximal end of pull wire 144, and second cavity 139 may be sized, shaped, and/or otherwise configured to receive second crimp 148 for securely coupling pull wire 144 to first housing 132 (and second housing 134 when second crimp 148 is received within the corresponding second cavity 139 of second housing 134). In this instance, second cavity 139 may allow for longitudinal translation of second crimp 148 relative to first body 102 (and second body 104) in response to a corresponding translation of actuator 130 relative to bodies 102, 104, such that pull wire 144 may be longitudinally movable relative to channels 124. In some embodiments, second crimp 14 may have a squared and/or rectangular cross-sectional profile that corresponds to a cross-sectional profile of second cavities 139, such that second crimp 148 is retained within second cavity 139 and inhibited from moving into channel 124. In some embodiments, one or more of first crimp 142 and second crimp 148 may include an aluminum crimp.

Still referring to FIG. 5A, biasing mechanism 146 may be disposed about the portion of pull wire 144 that extends proximally outwards from a proximalmost end of shaft 141. In some embodiments, biasing mechanism 146 may be coupled between an interior surface of first body 102 and second body 104, such as within channels 124, and a surface of first housing 132 and second housing 134 of actuator 130. Biasing mechanism 146 may be configured to position actuator 130 along a distal and/or intermediate portion of rails 122 when in an expanded (default) state. In this instance, medical device 100 and medical tool 140 may collectively form a medical system 10 for use in treating the subject.

Biasing mechanism 146 may be configured to maintain pull wire 144, which is coupled to actuator 130 via second cavity 139, in a first (distal) position absent an application of force onto actuator 130. With shaft 141, pull wire 144, and biasing mechanism 146 positioned within channel 124 of first body 102, medical device 100 may be transitioned from an open configuration to a partially closed configuration in response to moving first body 102 and second body 104 towards one another. For example, as seen in FIG. 5B, first body 102 and second body 104 may be moved about joints 114 (for example, one of first body 102 or second body 104 may be pivoted with respect to the other of first body 102 or second body 104 about joints 114). As described in detail above, the one or more alignment mechanisms (e.g., channel(s) 126, protrusion(s) 128, alignment mechanism(s) 135) may be configured to facilitate alignment of first body 102 and second body 104 to one another, and first housing 132 and second housing 134 to one another, as medical device 100 transitions between the open configuration (FIG. 5A), the partially closed configuration (FIG. 5B), and the closed configuration (FIG. 5C).

As seen in FIG. 5B, medical tool 140 may include end effector 150 at a distal end of shaft 141. End effector 150 may be coupled to pull wire 144, such that movement of pull wire 144, which may be caused by a corresponding movement of actuator 130, may provide for an actuation of end effector 150. It should be appreciated that first housing 132 and second housing 134 may be configured to move simultaneously over first body 102 and second body 104, respectively, when actuator 130 is in the assembled state and moved proximally and/or distally due to an engagement between guides 136 and rails 122. As described above, pull wire 144 may extend through shaft 141, such that a distal end of pull wire 144 (not shown) may be coupled to end effector 150. In examples, end effector 150 may include biopsy forces, hemostasis clips, or any other suitable mechanism. In some embodiments, shaft 141 may be sized, shaped, and/or otherwise configured to be received through an esophagus of a subject (e.g., via a working channel of an endoscope) for positioning end effector 150 at the target treatment site.

Although medical tool 140 is discussed herein as including shaft 141 and end effector 150, this disclosure is not so limited such that medical tool 140 may include various scopes, sheaths, catheters, or other suitable insertion devices. Further, although the disclosure may refer at different points to an endoscopic procedure, it should be appreciated that medical device 100 may be used in connection with various other procedures for treating other target treatment sites within a subject's body.

Referring now to FIG. 5C, medical device 100 may be moved to the closed configuration in which first body 102 is coupled to second body 104 via a continued movement of first body 102 and second body 104 towards one another about joints 114. First body 102 and second body 104 may be securely attached to another upon the engagement of the pair of locking mechanisms 116, as described above. With medical tool 140 coupled thereto, medical device 100 may be configured and operable to control actuation of medical tool 140, and particularly end effector 150. For example, upon positioning end effector 150 at the target treatment site within the subject, actuation of actuator 130 may provide for a corresponding actuation of end effector 150 via movement of pull wire 144 relative to shaft 141.

As described above, with second crimp 148 received within second cavity 139, pull wire 144 may be coupled to actuator 130 such that movement of actuator 130 may provide for a corresponding movement of pull wire 144. For example, moving actuator 130 proximally from a first (distalmost) position towards a second (proximalmost) position along rails 122 may cause a corresponding proximal translation of pull wire 144 relative to shaft 141 and channel 124. Additionally, proximal movement of actuator 130 may be configured to move and/or compress biasing mechanism 146, such that biasing mechanism 146 may generate a resistive force against the proximal movement of actuator 130. In embodiments where end effector 150 may include forceps and/or clips, actuator 130 may be configured to cause the forceps and/or clips to move (e.g., open, close, etc.) in response to pulling pull wire 144 proximally.

Biasing mechanism 146 may be configured to urge actuator 130 from the second (proximalmost) position along rails 122 to the first (distalmost) position along rails 122, such that removal of a proximal (pulling) force onto actuator 130 may allow biasing mechanism 146 to return actuator 130 to the first (distalmost) position. In other words, biasing mechanism 146 may be configured to bias actuator 130 distally and end effector 150 to an unactuated state. Upon concluding use of medical tool 140 in a procedure, medical device 100 may be moved from the closed configuration to the open configuration (FIG. 5A) by disengaging the pair of locking mechanisms 116 (e.g., by unclipping snap locks 118 from respective ledges 120), thereby allowing removal of medical tool 140 from between first body 102 and second body 104.

Particularly, shaft 141 and pull wire 144 may be removed from channel 124 by decoupling first crimp 142 from first cavity 125 and second crimp 148 from second cavity 139. In this instance, medical tool 140 may be disposed and medical device 100 may be sterilized prior to its subsequent use with another medical tool in one or more additional procedures.

It should be appreciated that actuator 130, and particularly each of first housing 132 and second housing 134, may remain coupled to first body 102 and second body 104, respectively, when medical device 100 is in the open configuration and the closed configuration. For example, rails 122 may retain guides 136 therein, thereby causing first housing 132 and second housing 134 to remain coupled to respective first body 102 and second body 104. In the embodiment, actuator 130 may only be configured and operable to actuate end effector 150 without causing a corresponding movement of shaft 141 (e.g., may only be configured to move pull wire 144). In other embodiments, actuator 130 or other elements of medical device 100 may be configured and operable to move shaft 141 (e.g., translate, rotate, articulate, pivot, bend, deflect, etc.) in addition to actuating end effector 150.

Figure 6:
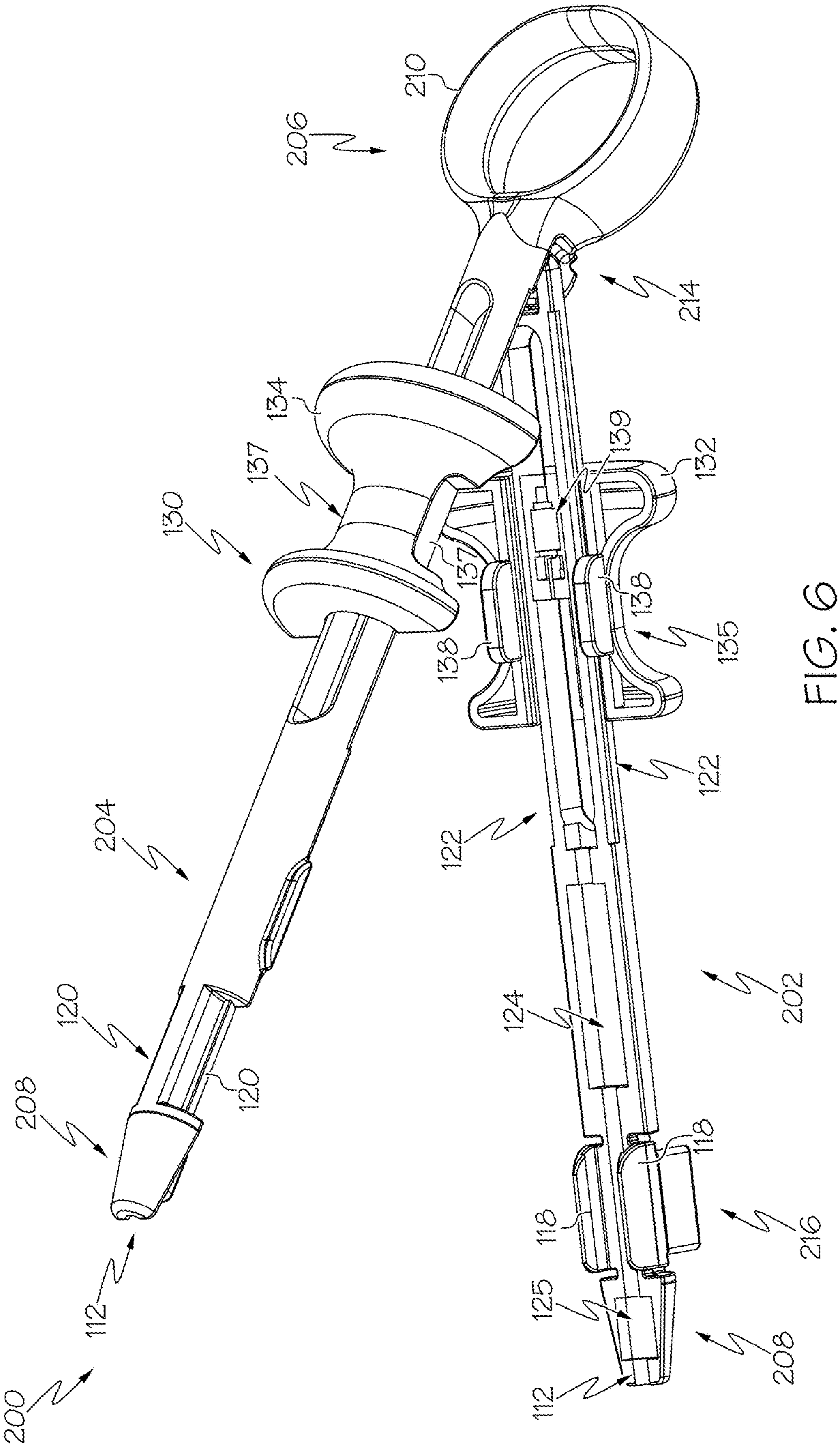
FIG. 6 shows a perspective view of another exemplary medical device, according to some embodiments.

Referring now to FIG. 6, another exemplary medical device 200 is depicted. Medical device 200 may be substantially similar to medical device 100 shown and described above except for the differences explicitly noted. As such, like reference numerals are used to identify like components. Accordingly, medical device 200 may be configured and operable similar to medical device 100.

Medical device 200 may include a first body 202 and a second body 204 that are movably coupled to one another about a joint 214. Joint 114 may be positioned adjacent to a proximal end 206. Joint 214 may include a hinge defining a single pivot point between first body 202 and second body 204. Thus, first body 202 and second body 204 may be configured to move relative to one another about the single pivot point defined at joint 214. In some embodiments, the hinge of joint 214 may be disengaged, such as by removing a pin (not shown) from joint 214, thereby allowing first body 202 and second body 204 to detach from one another, such as for purposes of cleaning medical device 200. First body 202 and second body 204 may be reattached to one another by reinserting the pin into the hinge of joint 214, thereby recoupling first body 202 and second body 204 at joint 214. As opposed to medical device 100, in which joints 114 may be pivotable/rotatable about one or more axes that are approximately parallel to the central longitudinal axis of medical device 100, joint 214 may be pivotable/rotatable about an axis that is transverse to (e.g., approximately perpendicular to) a central longitudinal axis of medical device 200.

In the example, first body 202 may not have a handle interface and second body 204 may include a handle interface 210 (e.g., a thumb aperture) at proximal end 206. As such, medical device 200 may only include a single handle interface 210. As shown in FIG. 6, joint 214 may be proximal to and adjacent to handle interface 210 of second body 204 and may be at a proximalmost end of first body 202.

Still referring to FIG. 6, medical device 200 may include a locking mechanism 216 for securely coupling first body 202 to second body 204. In the example, medical device 200 may include a single locking mechanism 216 positioned adjacent to a distal end 208. Locking mechanism 216 may include a pair of snap locks 118 on first body 202 and a pair of ledges 120 on second body 204. The pair of snap locks 118 may each be sized, shaped, and/or otherwise configured to engage and/or snap onto the corresponding ledge 120, and each of the pair of ledges 120 may be sized, shaped, and/or otherwise configured to receive the corresponding snap lock 118 for securely coupling first body 202 and second body 204 to one another. A position of locking mechanism 216 is merely exemplary, and medical device 200 may include multiple locking mechanisms 216 along a length of medical device 200.

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

What is claimed is:

1. A medical device comprising:

a handle including a first body and a second body that are joined at a hinge, wherein the first body is pivotable relative to the second body about the hinge; and an actuator including a first housing movably coupled to the first body and a second housing movably coupled to the second body;

wherein the medical device is configured to move between an open configuration in which the first body is at least partially decoupled from the second body and the first housing is at least partially decoupled from the second housing, and a closed configuration in which the first body is coupled to the second body and the first housing is coupled to the second housing.

2. The medical device of claim 1, wherein the first body and the second body collectively define a channel that is configured to receive a medical tool when the medical device is in the open configuration.

3. The medical device of claim 2, wherein the medical tool is securely attached inside the channel between the first body and the second body when the medical device is in the closed configuration.

4. The medical device of claim 3, wherein an end effector of the medical tool is movably coupled to the actuator when the medical tool is received within the channel and the medical device is in the closed configuration.

5. The medical device of claim 4, wherein the actuator is configured to actuate the end effector in response to the first housing and the second housing moving simultaneously along the first body and the second body.

6. The medical device of claim 5, wherein the end effector is configured to move in response to the actuator translating along the first body and the second body.

7. The medical device of claim 1, wherein the hinge is a first hinge, wherein the medical device includes a second hinge, wherein the first hinge and the second hinge are collectively configured to pivot the first body and the second body relative to one another.

8. The medical device of claim 7, wherein the first hinge is positioned proximate to a proximal end of the first body and the second body relative to the second hinge, and the second hinge is positioned proximate to a distal end of the first body and the second body relative to the first hinge.

9. The medical device of claim 1, further including a first locking mechanism configured to couple the first body and the second body to one another, thereby securing the medical device to the closed configuration.

10. The medical device of claim 9, wherein the first locking mechanism includes a snap lock positioned on the first body and a ledge positioned on the second body, the snap lock is configured to engage the ledge to couple the first body to the second body.

11. The medical device of claim 9, further including:

a second locking mechanism that is configured to couple the first body and the second body to one another, thereby securing the medical device to the closed configuration.

12. The medical device of claim 11, wherein the first locking mechanism is positioned proximate to a proximal end of the first body and the second body relative to the second locking mechanism, and the second locking mechanism is positioned proximate to a distal end of the first body and the second body relative to the first locking mechanism.

13. A medical device comprising:

a first handle body;

a second handle body movably coupled to the first handle body, wherein at least one joint defines a pivot point between the first handle body and the second handle body;

a first actuator housing disposed about and movably coupled to the first handle body; and a second actuator housing disposed about and movably coupled to the second handle body;

wherein the first handle body and the second handle body define a handle of the medical device, and the first actuator housing and the second actuator housing define an actuator of the medical device; and wherein the first handle body is at least partially separated from the second handle body and the first actuator housing is at least partially separated from the second actuator housing when the medical device is in an open configuration, and the first handle body is engaged with the second handle body and the first actuator housing is engaged with the second actuator housing when the medical device is in a closed configuration, wherein the at least one joint is configured to pivot the first handle body relative to the second handle body about the pivot point as the medical device moves between the open configuration and the closed configuration.

14. The medical device of claim 13, wherein the medical device is configured to receive a medical tool between the first handle body and the second handle body when in the open configuration; and wherein the medical device is configured to securely attach the medical tool to the first handle body and the second handle body when in the closed configuration.

15. The medical device of claim 14, wherein the actuator is configured to actuate the medical tool in response to the first actuator housing moving relative to the first handle body and the second actuator housing moving relative to the second handle body.

16. The medical device of claim 13, further including at least one locking mechanism configured to attach the first handle body to the second handle body as the medical device is moved to the closed configuration.

17. A medical device comprising:

a handle including a first body and a second body that are movable relative to one another; and an actuator including a first housing movably coupled to the first body and a second housing movably coupled to the second body;

wherein the medical device is configured to move between an open configuration in which the first body is at least partially decoupled from the second body and the first housing is at least partially decoupled from the second housing, and a closed configuration in which the first body is coupled to the second body and the first housing is coupled to the second housing, wherein an end effector of a medical tool is coupled to the actuator, wherein the actuator is configured to actuate the end effector of the medical tool in response to the first housing and the second housing moving simultaneously along the first body and the second body.

18. The medical device of claim 17, wherein the first body and the second body collectively define a channel that is configured to receive the medical tool when the medical device is in the open configuration.

19. The medical device of claim 18, wherein the medical tool is securely attached inside the channel between the first body and the second body when the medical device is in the closed configuration.

20. The medical device of claim 17, wherein the end effector is configured to move in response to the actuator translating along the first body and the second body.

* * * * *